United States Patent [19]
Fuller

[11] Patent Number: 6,130,080
[45] Date of Patent: Oct. 10, 2000

[54] ROLLER BOTTLE HAVING PITTED OR CRATERED INNER SURFACE FOR CELL GROWTH

[75] Inventor: Jess Paul Fuller, Ashby-de-la-Zouch, United Kingdom

[73] Assignee: Ashby Scientific, Inc., United Kingdom

[21] Appl. No.: 09/029,539

[22] PCT Filed: Aug. 23, 1996

[86] PCT No.: PCT/GB96/02070

§ 371 Date: Feb. 27, 1998

§ 102(e) Date: Feb. 27, 1998

[87] PCT Pub. No.: WO97/08291

PCT Pub. Date: Mar. 6, 1997

[30] Foreign Application Priority Data

Aug. 31, 1995 [GB] United Kingdom .................... 9517717
Dec. 20, 1995 [GB] United Kingdom .................... 9526032

[51] Int. Cl.[7] .............................. C12M 3/00; C12N 1/00; C12N 5/00; C12N 5/02
[52] U.S. Cl. ................... 435/243; 435/287.1; 435/288.1; 435/325; 435/394; 435/395; 435/410
[58] Field of Search .................... 435/243, 287, 435/288, 287.1, 288.1, 394, 395, 325, 410

[56] References Cited

U.S. PATENT DOCUMENTS 3,976,547  8/1976  McAleer et al. ................... 195/127
4,407,954 10/1983  Clyde ........................ 435/161
4,689,301  8/1987  Adet et al. ...................... 435/284

FOREIGN PATENT DOCUMENTS 0175286  3/1986  European Pat. Off. .
0300867  1/1989  European Pat. Off. .
0345415 12/1989  European Pat. Off. .
0394713 10/1990  European Pat. Off. .
0552412A1 7/1993  European Pat. Off. .
0614967A2 9/1994  European Pat. Off. .
3105861A1 9/1982  Germany .
1092634 11/1967  United Kingdom .
2268187A  1/1994  United Kingdom .
WO972347A of 0000 WIPO .

*Primary Examiner*—David M. Naff
*Assistant Examiner*—Deborah K. Ware
*Attorney, Agent, or Firm*—Wolf, Greenfield & Sacks, P.C.

[57] ABSTRACT

A roller bottle and method of culturing biological material, such as cells, using the roller bottle are disclosed. The roller bottle comprises a rough or uneven polymeric inner cell growth surface for culturing the cells. The growth surface is formed as an integral part of the roller bottle. The rough or uneven growth surface is provided by the inner growth surface being pitted or cratered to a depth of 1 mm or less. Further, the craters of the inner growth surface may be in the form of micro-cupels and measure less than 2 mm across.

20 Claims, 2 Drawing Sheets

ROLLER BOTTLE HAVING PITTED OR CRATERED INNER SURFACE FOR CELL GROWTH

BACKGROUND OF THE INVENTION

The present invention relates to vessels having textured surfaces for growing animal cells, plant cells, micro-organisms and the like ('bio-substances') and to methods for their production.

Many bio-substances can be propagated in vitro in containers such as so-called 'roller bottles', that is, cylindrical vessels, usually of glass or polystyrene, which are partially filled with a liquid medium comprising the bio-substances. The bottles are arranged to be rotated slowly about their longitudinal axes, promoting aeration, while the liquid medium provides nutrients to the bio-substances as they grow on the inner surfaces of the container.

Limitations in the efficiency of conventional procedures have hitherto been due to the relatively small surface area provided by the smooth interior of the container, as well as the fact that such surfaces do not provide optimum characteristics for the growth processes. It is an object of the present invention to eliminate or minimise these disadvantages.

SUMMARY OF THE INVENTION

Accordingly, in a first aspect of the invention, there is provided apparatus for use in a method of culturing micro-biological material, wherein said apparatus defines a rough or uneven growth surface arranged for contact with micro-biological material being cultured. An advantage of the inventive apparatus is that its use can allow cultured material to be grown at enhanced rates.

Preferably, the growth surface is rendered rough or uneven by surface features having a depth of 1 mm or less and, preferably, a depth of 0.1–0.5 mm. In preferred embodiments, the growth surface is pitted, or pockmarked with a plurality of craters or crater like depressions, preferably to depths of 1 mm or less and more preferably to depths of 0.1–0.5 mm. Preferably, the craters or crater like depressions measure less than 5, preferably less than 2, and more preferably less than 1 mm across. Most preferably, the crater or crater like depressions measure less than 0.5 mm across.

In further embodiments, the growth surface is micro-cupellated and it can be formed from an organic polymer. The polymer can be coated onto a supporting substrate and, preferably, is a silicone rubber. In an embodiment, the growth surface forms an inner surface of a container for retaining biological material being cultured.

In a second aspect, the invention provides a method of culturing a micro-biological material, comprising culturing said material using apparatus defining a growth surface, wherein said material is in contact with the growth surface and the growth surface is uneven or rough. Advantageously the inventive method allows biological material to be grown at an enhanced rate.

Preferably, the apparatus employed in the second aspect of the invention is in accordance with its first aspect.

In a third aspect, the invention provides a method of providing a substrate with a textured surface comprising the steps of forming a mobile surface studded with a granular material on the substrate, setting the mobile surface and removing the granular material to leave a textured surface on said substrate.

In a fourth aspect of the invention, there is provided an article having a textured surface that can be obtained by a method according to the invention in its third aspect. Preferably, the article is a tissue or cell culture vessel, such as a roller-bottle.

In all aspects of the invention the biological material preferably comprises tissue, cells or like matter, including viral particles or virions.

In the invention according to its fourth aspect, the mobile surface is preferably tacky prior to the setting step, so as to promote adherence of the granular material. In a preferred embodiment, a (preferably solvent-less) silicone paint, designed for polymerisation to form silicone rubber, is applied to the interior surface of a glass or polystyrene roller bottle. While the coating is still in liquid form, common salt particles are injected into the container, for example, under pressure, to adhere to the prepared silicone coating, with any excess salt being removed again from the container. The coating is then allowed to polymerise into a solid layer at ambient or elevated temperature, depending on the type of silicone used. When hardened, the salt particles adhering to the coating are removed by dissolution in water, to leave a surface-porous layer exhibiting a cratered or micro-cupellated structure, as well as the special affinity for bio-substances of silicone rubber. The container so prepared is found to result in a greatly increased yield when used for growth processes in the manner described.

To promote adhesion of the silicone rubber layer within a glass or polystyrene container, a conventional adhesive, preferably a mineral spirit based primer, can be first applied to the surface prior to deposition of the silicone layer.

In embodiments of the invention, it is a pre-requisite that the growth surface should be non-toxic and inert in respect of bio-substances and liquid media. The method of creating such surfaces should not involve any materials, which if remaining on the surface as impurities, could have a deleterious effect on the growth process.

In the above described method, various types of particles can be used in place of common salt, such as, for example, sugar, saltpetre and the like; however, common salt is preferred as being non-toxic and inert in respect of normal media and bio-substances, as well as being soluble in water for subsequent removal. Solubility of the particles in a non-toxic solvent is an important factor in their choice.

Attempts have been made to use 'open-porous' silicone rubbers, such as the material 'Immobasil' ('Immobasil' is a registered trade mark); however, the results obtained were not as satisfactory as those achievable using the various aspects of the present invention. The open-porous structure (that is, the presence of inter-connected pores within the body of the silicone rubber) in such known materials leads to difficulties in the subsequent harvesting of the biosubstances from the interstices of the coating on completion of a growth cycle.

In an embodiment of the invention, surface pitting or cratering, for example, micro-cupels, can be produced in the inner surfaces of glass or polystyrene containers per se. For this purpose, salt or other suitable particles are injected, for example, pneumatically, into the container while the latter is at elevated temperature, either during its manufacture or on subsequent heating. Upon cooling, the particles are then removed as described above, leaving the interior surface of the glass or polystyrene container with a textured, cratered or micro-cupellated structure, again resulting in enhanced efficiency of the process. In the case of polystyrene containers, prior to use, the standard procedure of plasma treatment of the inner surface can be applied to impart a negative electrical charge to the surface, as required for the growth process. Other types of particle can be used apart from-salt, the latter however, being again preferred for the reasons enumerated.

It is evident that other methods lying within the ambit of the invention may also be used to derive surface porous, cratered or micro-cupellated textured surfaces of the nature described for growing of bio-substances. The invention can equally be applied to all suitable containers, such as, for example, flasks, tubes, trays, roller bottles, plastic bags and the like.

In applications where very large area growth surfaces are required, it is conventional to utilise containers which comprise flat plates, for example, of polystyrene, wetted by the liquid medium, and upon which the bio-substances are made to grow. Such plates can also be provided with coatings of silicone rubber having a cratered or micro-cupellated, porous, surface structure according to the invention, in the manner described above, to result in substantially enhanced productivity.

Thus, roller bottles and other containers according to the invention can have a specially textured, cratered or micro-cupellated growth surface, usually an inner surface, suitable for use in the growth of bio-substances as aforesaid. By their nature, these surfaces are more conducive to the adhesion and growth of bio-substances, with resulting improved process efficiency. It is considered that the larger surface areas provided by such growth surfaces is a factor in their enhanced performance.

In order that the invention may be better understood, an example thereof will now be described by way of illustration only and with reference to the accompanying drawings, wherein:

DESCRIPTION OF THE INVENTION

Figure 1:
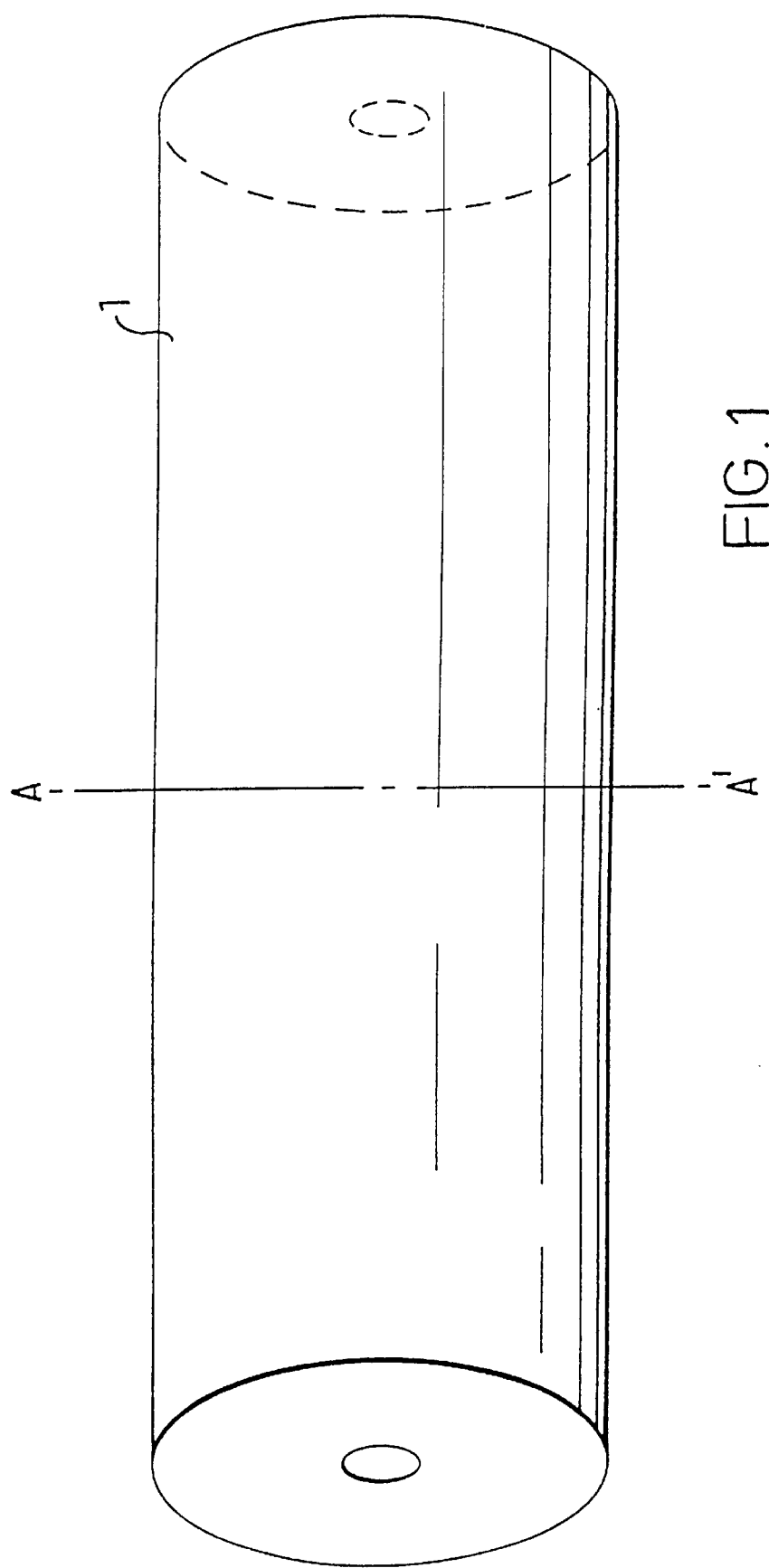
FIG. 1 is a schematic front perspective view of a conventional roller bottle.
Figure 2:
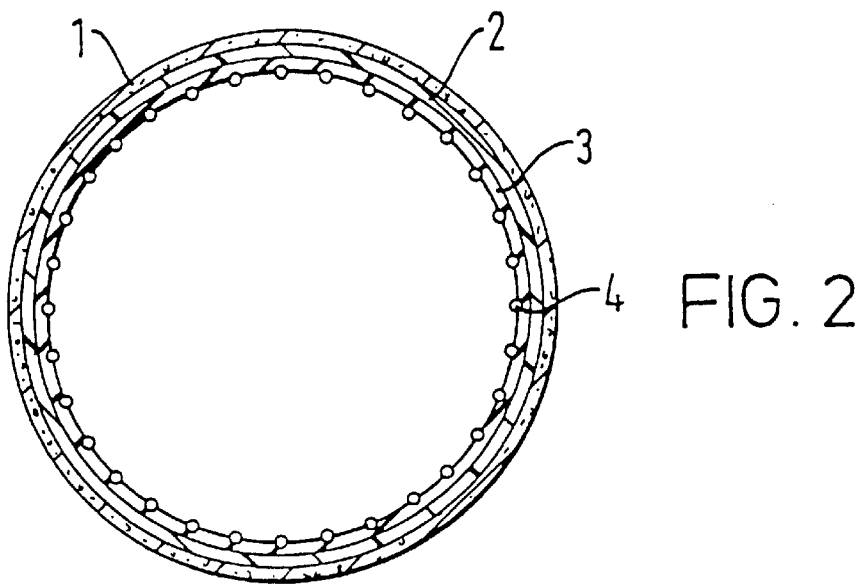
FIG. 2 is a schematic side cross-sectional view of the roller bottle of FIG. 1 along the line AA' after partial treatment by the inventive method.
Figure 3:
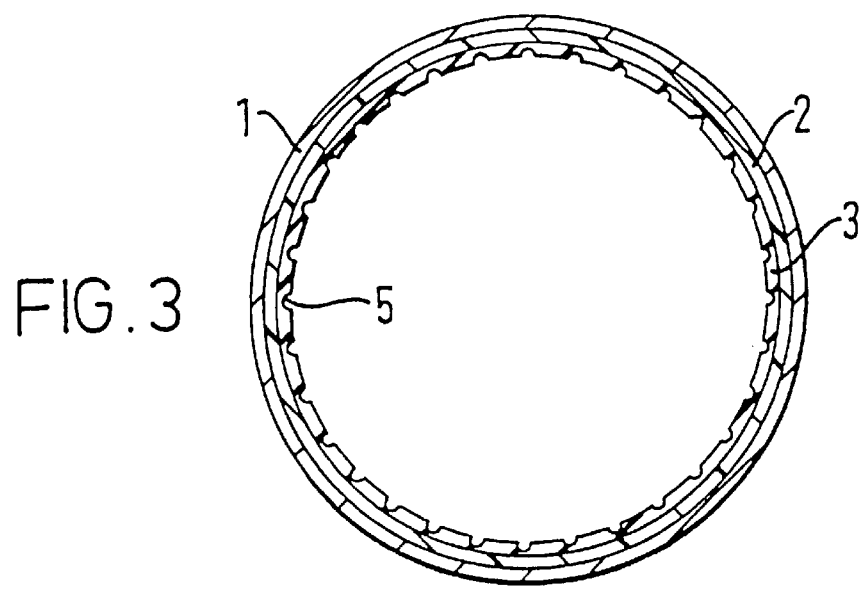
FIG. 3 is a schematic side cross-sectional view of the roller bottle of FIG. 2 after treatment by the inventive method has been completed.
Figure 4:
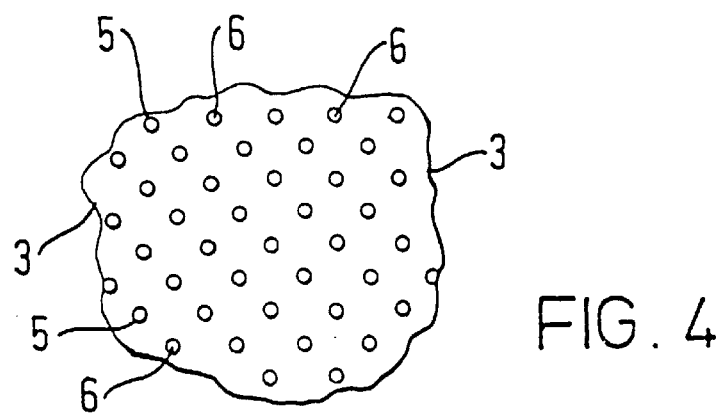
FIG. 4 is a schematic scrap view from a point on the axis of the roller bottle showing a portion of the growth surface after treatment by the inventive method has been completed.

With reference to FIGS. 1 to 4, a polystyrene roller bottle 1 is provided with a cratered or micro-cupellated surface according to the inventive method as follows. To the interior surface of bottle 1, a coating 2 of silicone rubber primer SS 4155 (General Electric Co., Connecticut, U.S.A.) is applied by brushing or other means and allowed to dry at 70° C. for 15 minutes. A coating 3 of silicone rubber paint PTV 118 (General Electric Co., Connecticut, U.S.A.), approximately 0.05 to 0.2 mm in thickness, is applied to primer coating 2 and left to stand for 1 minute. A substantial quantity of common salt 4 is then introduced into bottle 1 until approximately ⅓ full and the latter shaken, so that salt 4 adheres to all of the paint coating 3. The excess salt 4 is removed and coating 3 allowed to cure at 70° C. for 30 mins. Bottle 1 is then filled with boiling water and allowed to stand for 10 minutes before the water is removed. This last step is repeated once before bottle 1 is rinsed with isopropyl alcohol and left to dry at 70° C. for 30 mins. The resultant roller bottle 1 has a textured interior surface 5 provided by craters or micro-cupels 6 inset in silicone rubber layer 4.

The roller bottle 1 can then be inoculated with a biological material, for example cells taken from a commercially available cell line such as Madin Darby Canine Kidney, suspended in an appropriate commercially available nutrient medium, such as Glucose Minimum Essential Medium containing 5% foetal calf serum, selected for its suitability for growing the chosen cells. The roller bottle can then be placed upon conventional equipment designed to gently roll the bottle under conditions conducive to growing cells from the selected line. For example, a common culturing temperature is 37° C. After an appropriate culturing period, the growing cells can be harvested from the roller bottle using conventional techniques, such as trypsination or mechanical scraping.

What is claimed is:

1. A roller bottle for use in a method of culturing microbiological material, comprising a rough or uneven polymeric inner cell growth surface added to or formed as an integral part of the bottle, said inner growth surface being pitted or cratered to provide said rough or uneven growth surface and being arranged for contact with microbiological material being cultured.

2. A roller bottle as claimed in claim 1, wherein the inner growth surface is pitted or cratered to a depth of 1 mm or less.

3. A bottle as claimed in claim 2, wherein the inner growth surface is pitted or cratered to depths of 0.1–0.5 mm.

4. A roller bottle as claimed in claim 2, wherein craters of the cratered surface measure less than 2 mm across.

5. A roller bottle as claimed in claim 1, wherein craters of the cratered surface are in the from of micro-cupels.

6. A roller bottle as claimed in claim 1, wherein said polymer is a silicone rubber.

7. A method of culturing a microbiological material, comprising culturing said material in contact with an inner growth surface provided by a roller bottle as claimed in claim 1.

8. A roller bottle as claimed in claim 2, wherein craters of the cratered surface measure less than 1 mm across.

9. A roller bottle as claimed in claim 2, wherein craters of the cratered surface measure less than 0.5 mm across.

10. A method of providing a bottle with a rough or uneven growth surface for use in culturing microbiological material, comprising forming a layer of an organic polymer studded with a granular material on an inner surface of the bottle, setting the layer, and removing the granular material to leave a pitted or cratered inner surface as an integral part thereof.

11. A method as claimed in claim 10, wherein the polymer is silicone which is tacky prior to setting.

12. A method as claimed in claim 10, wherein the layer is formed by coating an inner surface of the bottle with a layer of a silicone surface-forming material and studding said layer with a granular material.

13. A method as claimed in claim 12, wherein the inner surface of the bottle is treated with an adhesive prior to coating with the layer of the silicone surface-forming material.

14. A method as claimed in claim 10, wherein the layer is formed by coating an inner surface of the bottle with a layer of a silicone surface-forming material in admixture with a granular material.

15. A method as claimed in claim 14, wherein the inner surface of the bottle is treated with an adhesive prior to coating with the layer of silicone surface-forming material.

16. A method as claimed in claim 10, wherein the bottle is made of glass or an organic polymer.

17. A method as claimed in claim 10, wherein the granular material is soluble and is removed by dissolution.

18. A method as claimed in claim 17, wherein the granular material is sucrose, salt or potassium nitrate.

19. A method as claimed in claim 10, wherein craters of the cratered surface are in the form of micro-cuples.

20. A roller bottle for use in culturing microbiological material obtainable by a method according to claim 10.

* * * * *